United States Patent [19]
Bader et al.

[11] Patent Number: 6,140,133
[45] Date of Patent: Oct. 31, 2000

[54] DEVICE AND PROCESS FOR SYNTHESIZING MACROMOLECULES

[75] Inventors: Raoul Bader, Ulm; Michael Hinz, Blaustein; Hartmut Seliger, Elchingen-Thalfingen, all of Germany; Robert Haener, Fehren, Switzerland

[73] Assignee: Novartis AG, Basel, Switzerland

[21] Appl. No.: 09/101,966

[22] PCT Filed: Jan. 20, 1997

[86] PCT No.: PCT/EP97/00236

§ 371 Date: Aug. 21, 1998

§ 102(e) Date: Aug. 21, 1998

[87] PCT Pub. No.: WO97/26986

PCT Pub. Date: Jul. 31, 1997

[30] Foreign Application Priority Data

Jan. 23, 1996 [DE] Germany ................. 196 02 159

[51] Int. Cl.[7] .................................................. B01J 19/00
[52] U.S. Cl. ...................... 436/180; 436/518; 422/100; 422/103; 422/131; 422/134
[58] Field of Search ................. 422/63, 100, 103, 422/104, 131, 134; 436/43, 174, 180, 518; 536/124, 126

[56] References Cited

U.S. PATENT DOCUMENTS

| | | | |
|---|---|---|---|
| 5,137,698 | 8/1992 | Ansorge et al. | 422/242 |
| 5,429,807 | 7/1995 | Matson et al. | 422/131 |
| 5,486,335 | 1/1996 | Wilding et al. | 422/55 |
| 5,580,523 | 12/1996 | Bard | 422/50 |
| 5,643,738 | 7/1997 | Zanzucchi et al. | 435/6 |
| 5,846,396 | 12/1998 | Zanzucchi et al. | 204/601 |
| 5,929,208 | 8/1992 | Heller et al. | 530/333 |

FOREIGN PATENT DOCUMENTS

| | | |
|---|---|---|
| 93/09668 | 5/1993 | WIPO . |
| 95/11748 | 5/1995 | WIPO . |

Primary Examiner—Long V. Le
Attorney, Agent, or Firm—David E. Wildman

[57] ABSTRACT

Provision is made, in a device and a process for the synthesis of macromolecules, for reagent solutions to be conveyed through reaction channels (15) which are connected to one another by intermediate channels (16, 17) and are preferably aligned parallel to one another, the reaction channels (15) being so displaced between individual synthesis steps relative to the carrier material acted on by the reagent solutions that, in the new position, the reaction channels (15) cover different synthesis zones from those in the previous position. In that manner provision is made for the synthesis of a large number of different sequences by relatively few synthesis steps.

20 Claims, 11 Drawing Sheets

DEVICE AND PROCESS FOR SYNTHESIZING MACROMOLECULES

The invention relates to a device for the synthesis of macromolecules, especially in sequentially homologous series, having at least one housing member comprising a number of reaction channels and having a further housing member comprising sealing portions with which the reaction channels can be covered over, in which device between the housing members a carrier material, which can be covered in synthesis zones by reaction channels, can be positioned in a number of different arrangements relative to the reaction channels.

The invention relates also to a process for the synthesis of macromolecules, especially in sequentially homologous series, in which reaction solutions are conveyed in synthesis zones over a carrier material by way of a number of reaction channels.

Such a device and such a process are known from WO 95/11748. The generic device has a number of reaction channels provided in a housing member, it being possible for a carrier material to be inserted between the housing member comprising the reaction channels and a further housing member comprising sealing portions that cover over the reaction channels. For the synthesis of macromolecules, different reagent solutions are conveyed through the reaction channels in a sequential order that is also variable.

After carrying out a succession of first synthesis steps in a first position, after which there are present in each of the synthesis zones covered by reaction channels macromolecules having first sequences of structural units, in further positioning steps the reaction channels are so rotated, for example through 90°, and possibly subsequently displaced linearly, that in the resulting new position they cover in cellular regions synthesis zones that were previously covered by other reaction channels. In a succession of further synthesis steps, further sequence portions of structural units can be added to the macromolecules formed in the cellular regions during the first synthesis steps.

Although the generic device and the generic process allow the formation of a two-dimensional field of macromolecules with a combination of portions having different sequences, the synthesis of macromolecules having different sequences is, of course, very complex in terms of apparatus because it requires a large number of reaction channels to be acted on by different reagent solutions, or alternatively, with an acceptable number of positioning steps and the proviso of as high as possible a sequence variation, the quantitative yield is relatively low because of the consequently relatively small cellular regions.

The problem underlying the invention is therefore to provide a device and a process of the kind mentioned at the outset that allows the synthesis of macromolecules having different sequences in a high yield using relatively simple apparatus.

The problem is solved in accordance with the invention, in a device of the kind mentioned at the outset, by the provision of intermediate channels by which a number of reaction channels are connected to one another.

The problem is solved in a process of the kind mentioned at the outset by the arrangement of reaction channels, which are connected to one another by intermediate channels, and the carrier material in different relative positions in different synthesis steps to cover synthesis zones.

The displacement of a carrier material relative to a chain of reaction channels that are connected to one another by intermediate channels by a distance that corresponds to the periodic spacing of the reaction channels or to a multiple thereof has the result, in the case where synthesis steps are carried out in succession at the individual positions, that oligomers having different sequences of structural units are formed in synthesis zones of large area, only one reaction solution having a single specific composition having been conveyed through the linked reaction channels in each synthesis step. As a result of the displacement of the reaction channels relative to, for example, directly adjacent synthesis zones that have already been acted on by reaction solutions of a different specific composition in preceding synthesis steps, it is possible by means of relatively few synthesis steps, in conjunction with positioning steps that displace the reaction channels relative to the carrier material, to produce a large number of macromolecules in which the sequences of individual structural units differ from one another. For example, to synthesise n oligomers having the same chain length m, all that is required is the number m+n−1 synthesis steps in conjunction with positioning steps that displace the reaction channels relative to the carrier material.

The reaction channels are preferably arranged parallel to and equidistant from one another. For efficient utilisation of the carrier material and with a view to a compact design of the device, it is advantageous for the spacing between reaction channels to be smaller than the width of the reaction channels.

In further developments of a first kind, the reaction channels are aligned at right angles to the direction of the relative displacement of the carrier material. In further developments of a second kind, the reaction channels are arranged at an angle to the direction of the relative displacement of the carrier material.

Referring to the arrangement of the intermediate channels, in a first group of embodiment examples provision is made for the intermediate channels to be arranged in the plane of the reaction channels and to be open at the side facing the carrier material. In such configurations, it is simple to produce the entire channel arrangement on one side of a housing member, for example by milling or impression moulding.

A second group of arrangements provides intermediate channels which, directed away from the carrier material, extend in the form of closed conduits from one reaction channel to another reaction channel, so that the carrier material is acted on by reagent solutions only in synthesis zones covered by reaction channels. A distinguishing characteristic of such an arrangement is that, in a manner that is favourable for further processing at a later stage, macromolecules are synthesised only in synthesis zones that are separated from one another.

It will be understood that the first and second kinds of embodiments having different alignments of the reaction channels in the direction of the relative displacement of the carrier material can in each case be combined with the different arrangements of the intermediate channels of the first and second groups of embodiment examples described above.

For a rapid synthesis of large amounts of macromolecules it is advantageous to provide a plurality of independent channel arrangements, each consisting of reaction channels and intermediate channels that are in communication with one another, which arrangements are arranged at one side and/or at both sides of the carrier material. With p channel arrangements, this results in a number of chain-lengthening steps of p (m+n−1). Advantageously, in the case of an arrangement at both sides, sealing portions are formed between reaction channels of one housing member in order to cover over reaction channels of another housing member.

In order to avoid dead-flow areas in the reaction channels and intermediate channels, the intermediate channels are advantageously connected to the ends of the reaction channels and have walls that are rounded off at the edges.

In order that the carrier material, which is advantageously elongate, can be guided reliably so as to enable exact positioning, advantageously one of the housing members to be brought into contact with the sample material has an elongate guide recess, and another housing member has a guide projection complementary to the guide recess, between which guides the carrier material can be inserted and, on displacement for carrying out a further synthesis step, displaced relatively, in a controlled manner, guided by the edges of the guide recess.

The macromolecules are so-called biomacromolecules, such as, for example, peptides or oligonucleotides, non-biological, structurally modified derivatives thereof, or synthetic macromolecules having no biological association.

Further expedient arrangements and advantages of the invention are the subject of the subclaims and of the following embodiment examples described with reference to the drawings in which:

Figure 1:
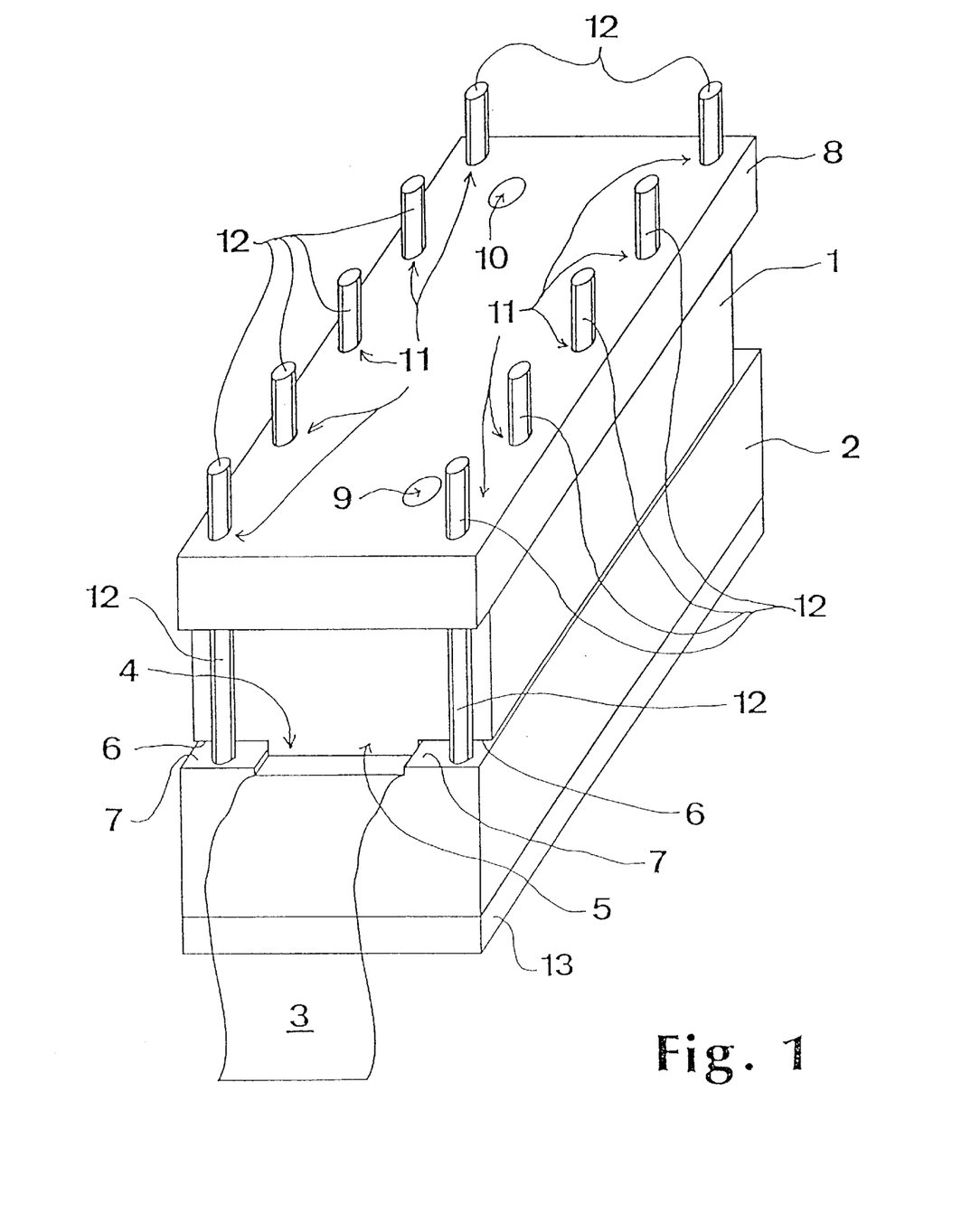
FIG. 1 is a perspective view of an embodiment example of a device for the synthesis of macromolecules having a carrier material arranged between housing members.

FIG. 1 is a perspective view of an embodiment example of a device for the synthesis of macromolecules. The device shown in FIG. 1 is provided with a first housing member 1 and a second housing member 2, which are cuboidal, and between those members an elongate carrier film 3 is positioned as carrier material in one of several arrangements. Advantageously, the carrier film 3 is made of polypropylene. In the embodiment example shown in FIG. 1, the first housing member 1 is provided with a guide projection 4, which extends in the longitudinal direction and which can be inserted, with the inclusion of the carrier film 3, into a guide recess 5 of complementary shape formed in the second housing member 2. Advantageously, in order to provide a seal the amount by which the guide projection 4 projects relative to the first side faces 6 at the outer sides of the first housing member 1, which amount is, for example, 2 mm, is greater than the depth of the guide recess 5 relative to the second side faces 7 at the outer sides of the second housing member 2, which is, for example, 1 mm.

Advantageously, the housing members 1, 2 are made of polytetrafluoroethylene (PTFE) or another plastically deformable plastics that is neutral towards the syntheses to be carried out. In modified embodiment examples, not shown, the housing members 1, 2 are made of metal, and elastic sealing elements made, for example, of silicone or PTFE, are used.

In the embodiment example shown in FIG. 1 a cover plate 8, into which a first synthesiser connection 9 and a second synthesiser connection 10 are inserted at the outer sides, is applied to that side of the first housing member 1 which is remote from the carrier film 3. A device (not shown in FIG. 1) for the automated supply and discharge of reagent-containing solvents, as reagent solutions for carrying out synthesis steps, and of rinsing solutions for the purpose of purification, may be connected as synthesiser to the synthesiser connections 9, 10.

The cover plate 8 also has a number of through-holes 11, through which threaded rods 12 can be inserted. The threaded rods 12 pass in corresponding through-holes through the housing members 1, 2 at the sides thereof and can be screwed into a base plate 13 which is arranged on the side of the second housing member 2 that is remote from the carrier film 3, the base plate being provided with corresponding internal threads. By screwing nuts (not shown in FIG. 1) onto the ends of the threaded rods 12 that project above the cover plate 8, the housing members 1, 2 can be brought to bear against one another with adjustable pressing forces and, for the relative positioning of the carrier film 3, can be separated from one another by loosening or unscrewing the nuts to release the seal.

In an arrangement that is modified with respect to the embodiment example shown in FIG. 1, instead of the threaded rods and nuts, articulated levers are provided which are attached to smooth-surfaced through-rods and are supported against the side of the cover plate 8 that is remote from the housing member 1, which levers make it possible for the housing members 1, 2 to be pressed together and released in an especially simply operable manner.

Figure 2:
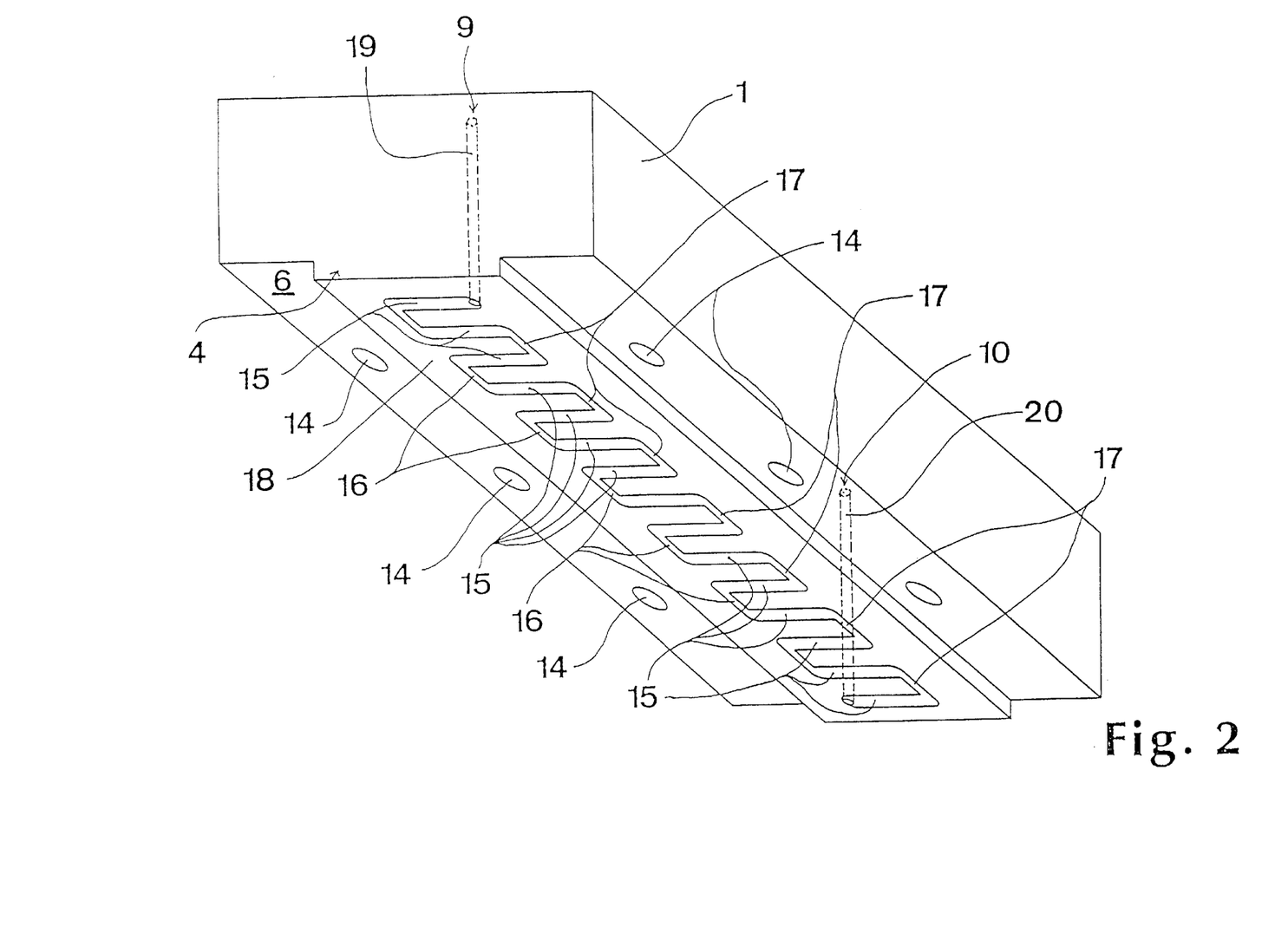
FIG. 2 is a perspective view of the housing member of the embodiment example according to FIG. 1, the housing member being provided with reaction channels and intermediate channels arranged in one plane in the shape of a meander.

FIG. 2 is a perspective view of the first housing member 1 of the device illustrated in FIG. 1 and shows the side that faces the carrier film 3; in this Figure, only some of the through-holes 14, which are arranged as extensions of the through-holes 11 in the cover plate 8, have been shown and given reference numerals. The first housing member 1 is provided in the region of the guide projection 4 with a meander-shaped arrangement of a number of reaction channels 15 that are, for example, 10 mm long, and of intermediate channels 16, 17, each of which connects two adjacent reaction channels 15 to one another; in the first housing member 1 according to FIG. 2, the reaction channels 15 and intermediate channels 16, 17 are arranged in a plane that is formed by a carrier-bearing face 18 of the guide projection 4 and are open at the side that faces the carrier film 3. The reaction channels 15 and intermediate channels 16, 17 are, for example, 0.3 mm deep. Each of a first group of intermediate channels 16 connects two adjacent reaction channels 15 by their ends arranged at the same side, while each of a second group of intermediate channels 17 connects two adjacent reaction channels 15 by their other ends, in such a manner as to produce an evenly meander-shaped arrangement of reaction channels 15 having an alternating sequence of intermediate channels 16, 17, of a width of, for example, 1 mm, extending between the ends of the reaction channels 15.

The first synthesiser connection 9 communicates via a first connection hole 19, having a diameter of, for example, 1 mm, with the closed end of the reaction channel 15 located at the front outer end in the illustration according to FIG. 2, while the second synthesiser connection 10, located at the rear end in the illustration according to FIG. 2, communicates via a second connection hole 20, having a diameter of, for example, 1 mm, to the closed end of the reaction channel 15 arranged at the other outer end.

Figure 3:
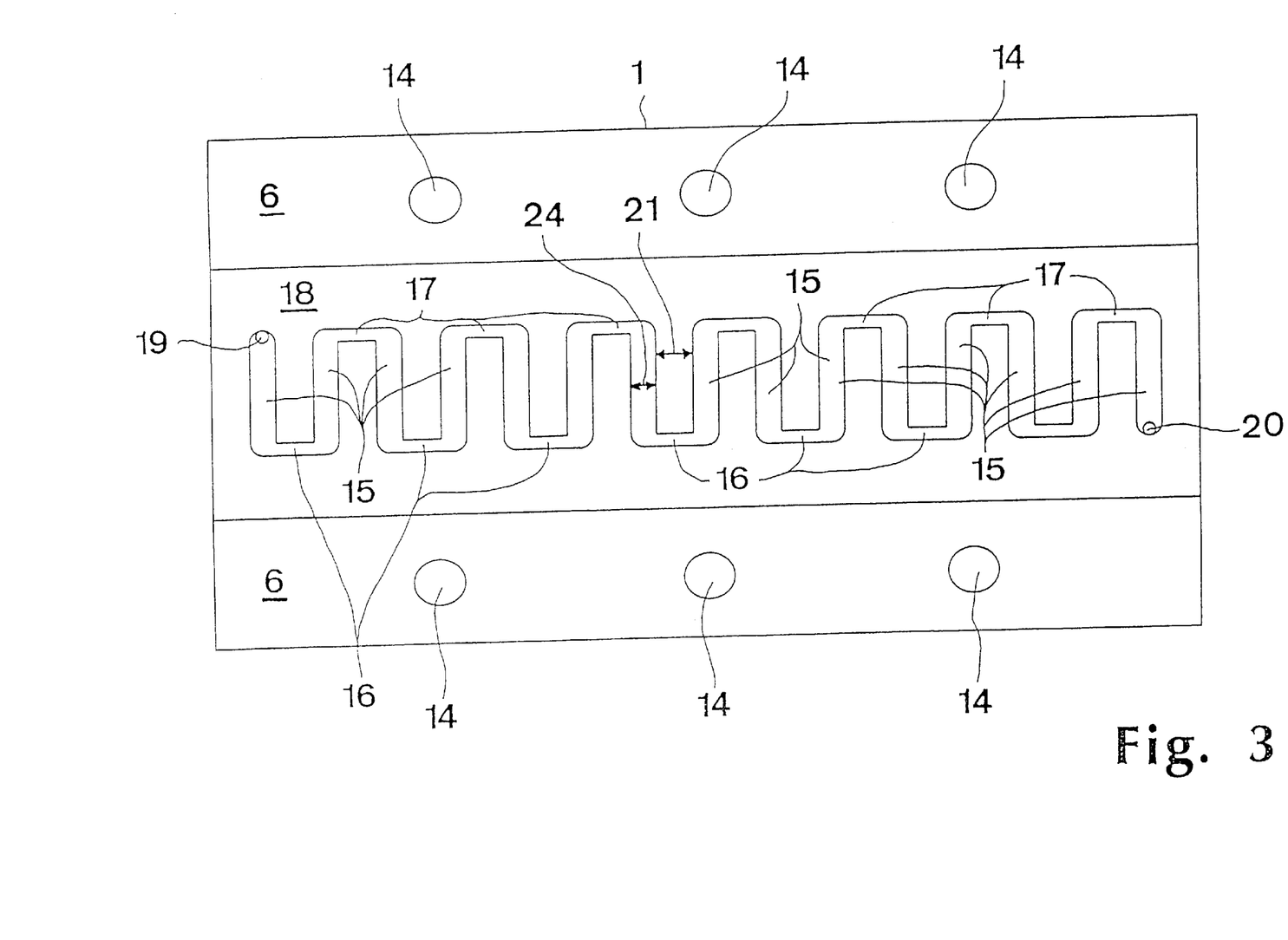
FIG. 3 is a plan view of the carrier-material-facing side of the housing member according to FIG. 2.

FIG. 3 shows the first housing member 1 according to FIG. 1 and FIG. 2 in plan view on the side that faces the carrier film 3. The reaction channels 15 are arranged parallel to one another and have identical spacings 21 between them of, for example, 3 mm. The reaction channels 15 extend substantially at right angles to the outer sides 22, 23, which are parallel to one another, of the guide projection 4, along which sides the carrier film 3 is displaceable in the longitudinal direction. The width 24 of each reaction channel 15 is the same and is, for example, 2 mm. On displacement of the carrier film 3 relative to the reaction channels 15 in the longitudinal direction by a distance corresponding to the sum of the spacing 21 between reaction channels and the width 24 of the reaction channels, that distance being, for example, 5 mm, given the measurements indicated by way of example above, or an integral multiple thereof, a number of reaction channels 15 come to rest over synthesis zones that have already been covered by reaction channels 15 in a previous position, while other reaction channels 15, located at the front end in the direction of displacement, cover new synthesis zones for the first time.

The reaction channels 15 provided in the embodiment example shown in FIG. 2 and FIG. 3 are of the same length, and are arranged with their ends in alignment so that the intermediate channels 16 and also the intermediate channels 17 are likewise in alignment with one another.

When the housing members 1, 2 are in the assembled position, the reaction channels 15 and the intermediate channels 16, 17 are sealed by sealing portions formed on the flat side of the guide recess 5, which side lies opposite to the carrier-bearing face 18, the sealing portions covering over the open sides of the reaction channels 15 and intermediate channels 16.

In an arrangement that has been modified with respect to the embodiment example illustrated by means of FIGS. 2 and 3, the reaction channels 15 are arranged at an oblique angle relative to the outer sides 22, 23 of the guide projection 4, the angle of inclination being the same for each reaction channel and each of the intermediate channels 16, 17 being in alignment. Given the same spacing of intermediate channels 16, 17 lying opposite to one another, in that configuration the area of the synthesis zones is larger than in a right-angled arrangement of the reaction channels 15.

Figure 4:
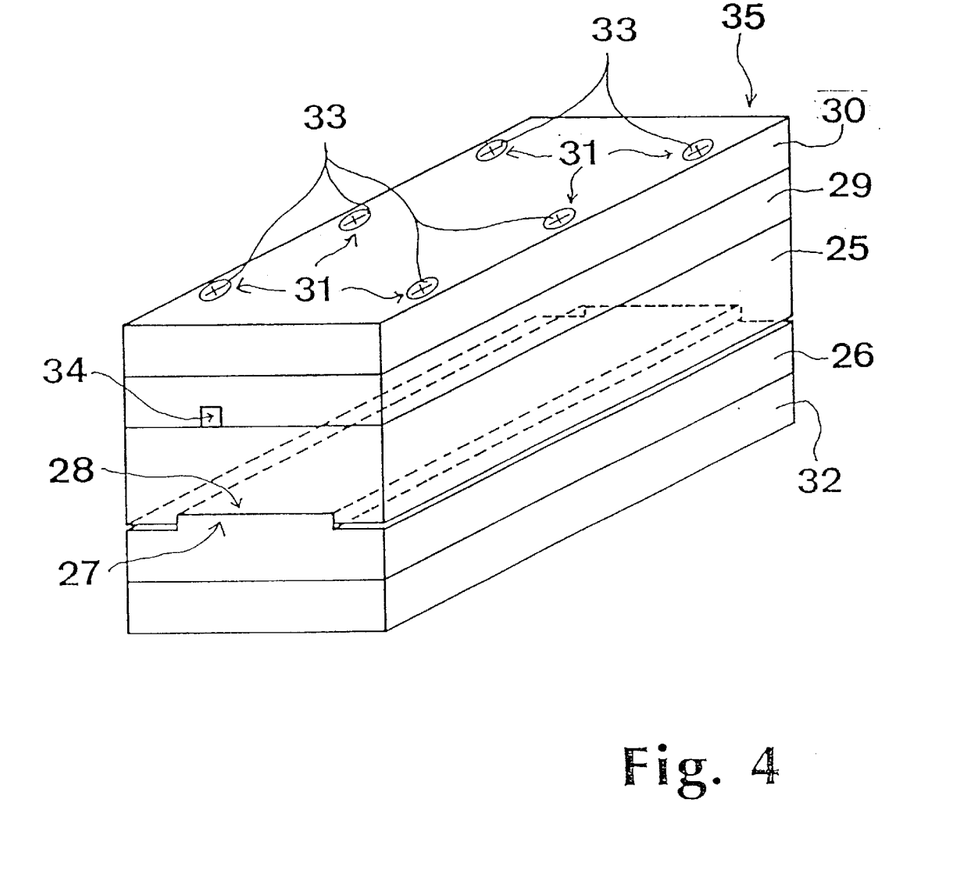
FIG. 4 is a perspective view of a further embodiment example of a device for the synthesis of macromolecules having housing members and a transfer member.

FIG. 4 is a perspective view of a further embodiment example of a device for the synthesis of macromolecules. The device shown in FIG. 4 is provided with a first housing member 25 and a second housing member 26, each of which is cuboidal and which can be joined to one another, with the engagement of a guide projection 27, which extends centrally in the longitudinal direction of the second housing member 26, in a guide recess 28, which is provided in the first housing member 25 and is of complementary shape to the guide projection 27, the amount by which the guide projection 27 projects being greater than the depth of the guide recess 28.

There is placed on the opposite side of the first housing member 25 to the second housing member 26 a transfer member 29, which in turn is covered on the opposite side to the first housing member 25 by a cover plate 30. The cover plate 30 has through-holes 31, which are provided at the outer sides in the longitudinal direction and with which there are aligned further through-holes, which extend through the transfer member 29 and the housing members 25, 26. Applied to the opposite side of the second housing member 26 from the first housing member 25 is a base plate 32, which is provided with threads that complete the through-holes. In the illustration according to FIG. 4, fixing screws 33 that pass through the through-holes are screwed into those threads in order to press together the housing members 25, 26. Furthermore, in the illustration according to FIG. 4 a first synthesiser connection 34 is provided at the front end face of the transfer member 29 and a second synthesiser connection 35 is provided at the rear end face.

Figure 5:
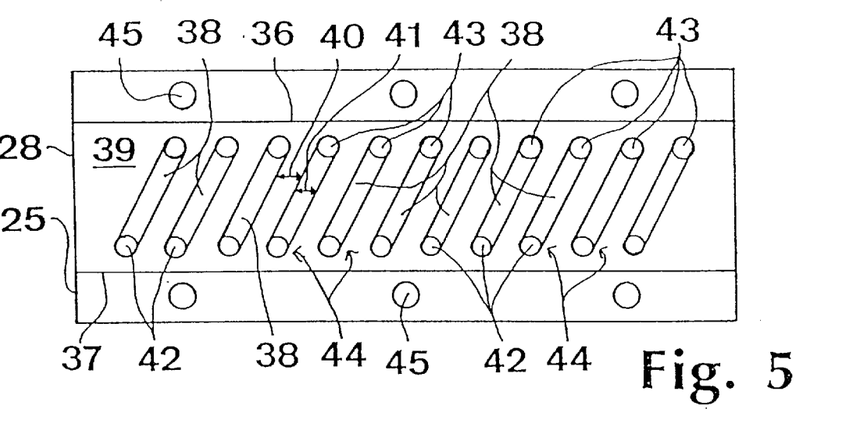
FIG. 5 is a plan view of the carrier-material-facing side of the housing member having reaction channels according to the embodiment example of FIG. 4.

FIG. 5 shows the first housing member 25 according to FIG. 4 in plan view on the side facing the second housing member 26. Reaction channels 38, arranged equidistantly apart and in parallel, are provided in the guide recess 28 at an oblique angle relative to the longitudinal parallel outer sides 36, 37, which channels are open towards the carrier-bearing face 39 facing the second housing member 26. The spacing 40 of the reaction channels, measured between facing outer sides of the reaction channels 38, together with the width 41 of the reaction channels, each measured in the longitudinal direction of the outer sides 36, 37, determine in accordance with the embodiment example shown in FIG. 3 the distance by which a carrier material inserted between the housing members 25, 26 needs to be displaced in order that synthesis zones are repeatedly exactly covered by reaction channels 38.

In the end regions of each of the reaction channels 38, ducts 42, 43 of intermediate channels 44 that form closed conduits open out. The ducts 42, 43 cross the first housing member 25 from the carrier-bearing face 39 to the side facing the transfer member 29. In the embodiment example shown in FIG. 5, the ducts 42, 43 are formed by round bores having a diameter that corresponds to the width of the reaction channels 38. Also shown in FIG. 5 are the through-holes 45 provided in the first housing member 25.

Figure 6:
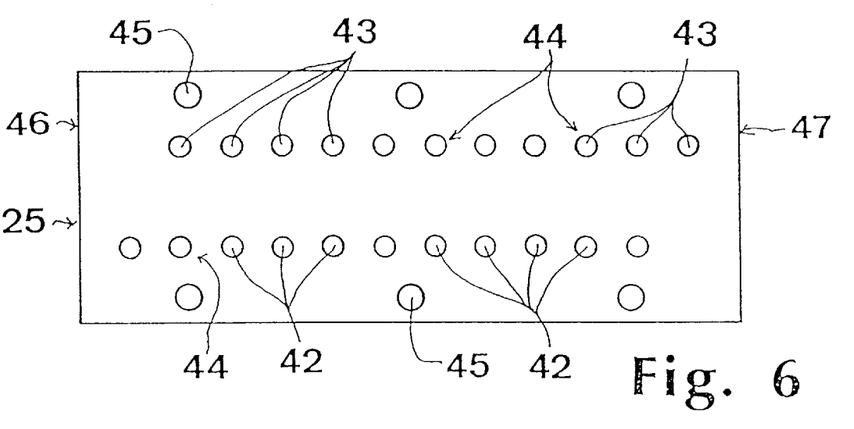
FIG. 6 shows the housing member according to FIG. 5 in plan view on the side facing the transfer member according to FIG. 4.

FIG. 6 is a plan view of the first housing member 25, shown in FIG. 5, on the side facing the transfer member 29. In the arrangement of the reaction channels 38 according to FIG. 5, the ducts 42, 43 extending through the first housing member 25 are arranged as a first group of ducts 43, arranged in alignment with one another in the longitudinal direction of the first housing member 25, and as a second group of ducts 43, arranged in alignment with one another in the longitudinal direction of the first housing member 25 and with the same spacing as the first group of ducts 42.

Furthermore, ducts 42, 43 associated with adjacent reaction channels 38 lie opposite to one another in the transverse direction parallel to the end faces 46, 47 of the first housing member 25. That arrangement of the ducts 42, 43, determined by the spacing 40 between the reaction channels, the width 41 of the reaction channels and the angle of inclination of the reaction channels 38, has the result that it is especially simple to provide bores for the production of the ducts 42, 43.

Figure 7:
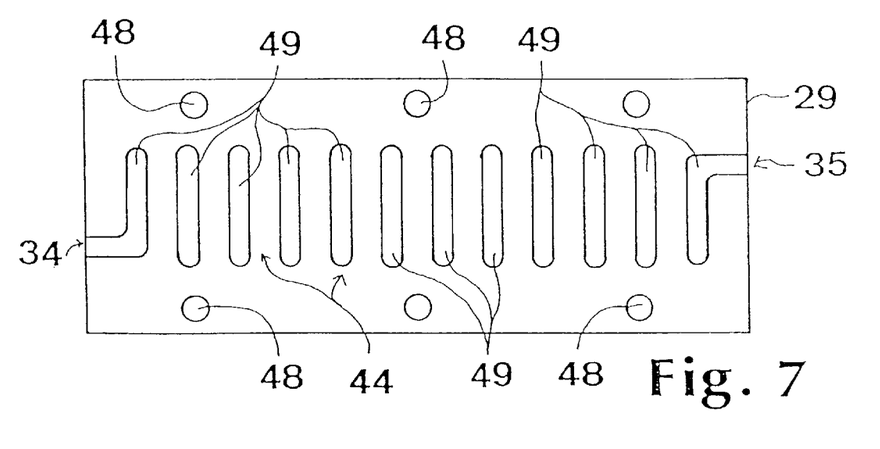
FIG. 7 shows the transfer member of the embodiment example according to FIG. 4 in plan view on the side facing the housing member shown in FIGS. 5 and 6.

FIG. 7 is a plan view of the side of the transfer member 29 facing the first housing member 25. That side of the transfer member 29, in addition to being provided with the through-holes 48, is provided with transfer holes 49, which extend between ducts 42, 43 lying opposite to one another in the transverse direction of the first housing member 25 and which are open on the side facing the first housing member 25 and form together with the ducts 42, 43 the intermediate channels 44. The transfer holes 49 have at the outer sides a longitudinal portion extending in the direction of the synthesiser connections 34, 35.

In a modification (not shown) of the embodiment example illustrated by means of FIGS. 4 to 7, the transfer holes between ducts 42, 43 are provided in the side of the first housing member remote from the reaction channels 38. It will be understood that both in the illustrated embodiment example and in the modification not shown, the transfer holes may extend between alternate pairs of ducts 42, 43 that are adjacent in the longitudinal direction.

Thus, in the embodiment example illustrated by means of FIGS. 4 to 7, intermediate channels 44 that span the reaction channels 38 in the manner of bridges are formed, those intermediate channels 44 extending outside the plane in which the reaction channels 38 are arranged, so that a three-dimensionally meander-like channel arrangement is formed in which macromolecules are synthesised, on a carrier film 3 as carrier material, only in the synthesis zones where the surface is covered by reaction channels 38. Since the synthesis zones covered by reaction channels 38 are completely separated from one another, an advantage of this embodiment example is that only the desired sequences of macromolecules are synthesised, which is not the case in the embodiment example illustrated by means of FIGS. 1 to 3 where, in a manner that may be disadvantageous for some applications, macromolecules that are differently constructed from those present in synthesis zones, having for example, sequence gaps, are synthesised in intermediate channels 16, 17.

Figure 8:
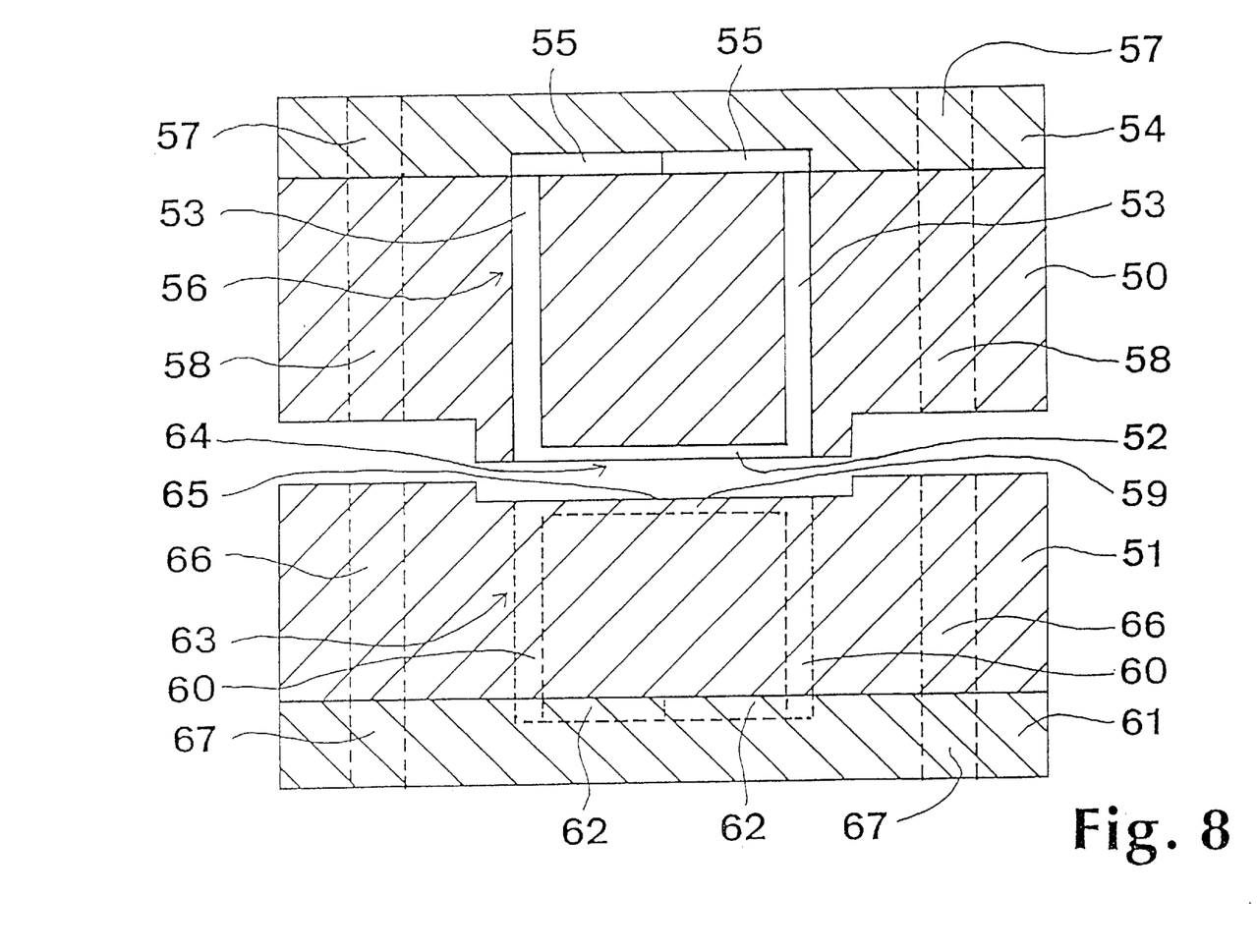
FIG. 8 is a sectional view of a further embodiment example of a device for the synthesis of macromolecules in which reaction channels are provided in two housing members that lie opposite one another.

FIG. 8 is a sectional view, in the transverse direction, of a further embodiment example of a device for the synthesis of macromolecules, which is provided with a first housing member 50 and a second housing member 51. The first housing member 50 of the embodiment example 5 shown in FIG. 8 is, corresponding to the first housing member 1 illustrated by means of FIGS. 2 and 3, provided with an arrangement of first reaction channels 52 that are parallel to one another and extend in the transverse direction and also, corresponding to the first housing member 25 illustrated by means of FIG. 5, with an arrangement of first ducts 53, the ends of which adjoin the first reaction channels 52 at right angles. In the illustration according to FIG. 8, a first transfer member 54 is positioned on the first housing member 50 on the side remote from the first reaction channels 52, which transfer member 54 is similarly constructed to the transfer member 29 illustrated by means of FIG. 7 but has first transfer holes 55 arranged at an oblique angle and extending at an angle for the purpose of connecting opposite ends of adjacent first reaction channels 52 in order to form, together with the first ducts 53, closed first intermediate channels 56.

Also provided in the first transfer member 54 and the first housing member 50 are through-holes 57, 58 which are in alignment with one another, for example to enable threaded rods or connecting screws to be passed through.

The second housing member 51 is cross-sectionally of similar structure to the second housing member 26 illustrated by means of FIGS. 4 and 5, but like the first housing member 50 is provided with second reaction channels 59 aligned parallel to one another in the transverse direction, the opposite ends of adjacent channels 59 being connected by means of second ducts 60 and by means of second transfer holes 62 that are provided in a second transfer member 61 arranged on the side opposite to the first housing member 50 and are open towards the second housing member 51, those ducts 60 and transfer holes 62 together forming second intermediate channels 63. In that arrangement, the first reaction channels 52 of the first housing member 50 and the second reaction channels 59 of the second housing member 51 are so spaced relative to one another and have such a width that the second reaction channels 59 can be covered over by first sealing portions 64 formed between the first reaction channels 52, and the first reaction channels 52 can be covered over by second sealing portions 65 formed between the second reaction channels 59.

Also provided in the second housing member 51 and in the second transfer member 61 are through-holes 66, 67 which are in alignment with one another and with the through-holes 57, 58 of the first transfer member 54 and of the first housing member 50.

Figure 9:
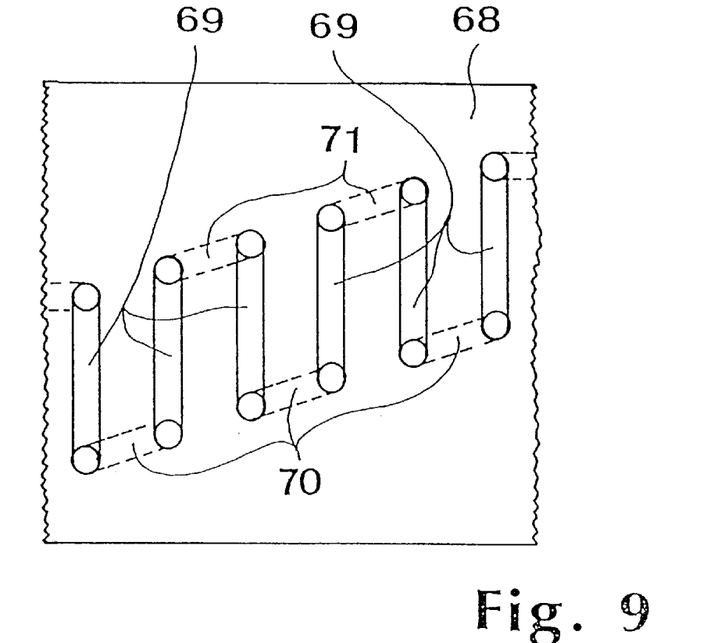
FIG. 9 is a plan view of the carrier-material-facing side of a housing member that is provided with reaction channels of the same length that are arranged displaced with respect to one another in their longitudinal direction.

The device illustrated by means of FIG. 8 is distinguished by the fact that for compact tasks macromolecules can be synthesised in an efficient manner at both sides of a carrier material using relatively few displacement steps for the positioning FIG. 9 is a plan view of a portion of a relatively flat housing member 68 of a device for the synthesis of macromolecules according to the invention in which reaction channels 69 that are arranged equidistantly apart and in parallel are provided, wherein the reaction channels 69 are displaced with respect to one another preferably by the same amount both in the transverse direction of the housing member 68 and the longitudinal direction of the reaction channels 69. Adjoining the ends of the reaction channels 59 in an alternating sequence are intermediate channels 70, 71 that connect reaction channels 69 by their ends located at the same side, which intermediate channels 70, 71 extend in the form of closed conduits outside the plane in which the reaction channels 69 are arranged. In the embodiment example shown in FIG. 9, the intermediate channels 70, 71 are formed by flexible plastics conduits that are chemically neutral towards the reagent solutions that are to be conveyed through them.

Figure 10:
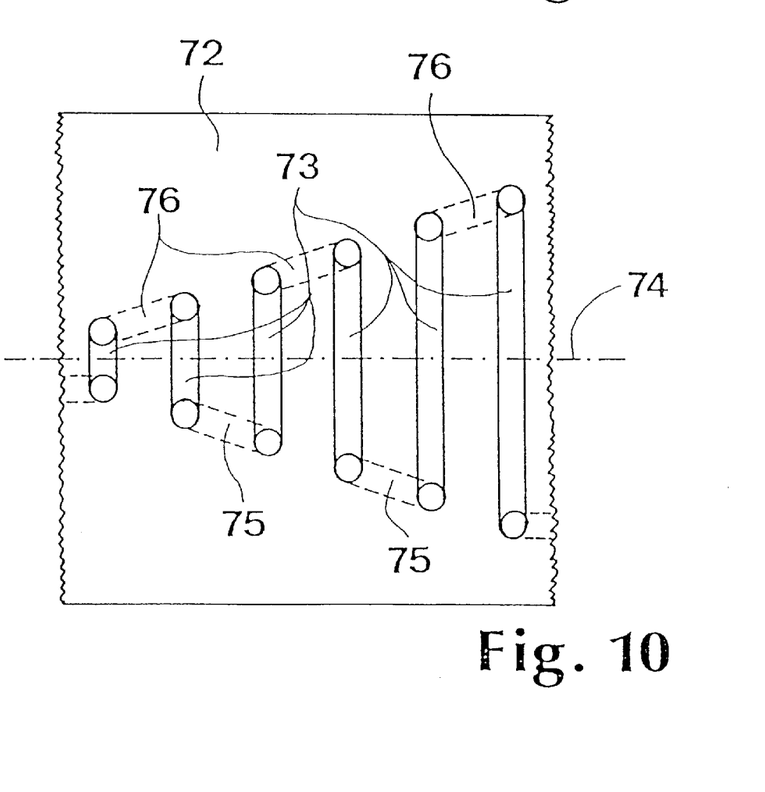
FIG. 10 is a plan view of the carrier-material-facing side of a further housing member that has reaction channels of different lengths.

FIG. 10 is a plan view of a portion of a further housing member 72 of a device for the synthesis of macromolecules according to the invention, which housing member has reaction channels 73 arranged equidistantly apart and in parallel which vary in length and are arranged preferably symmetrically relative to a central axis 74 of the housing member 72. In a similar manner to the embodiment example illustrated by means of FIG. 9, intermediate channels 75, 76 that open into the ends of the reaction channels 73 are connected to the reaction channels 73 in alternating sequence.

On positioned displacement of the reaction channels 69, 73 of the housing members 68, 72 relative to a carrier material with the synthesis zones being repeatedly covered, it is possible to synthesise macromolecules that each have an identical structure in an overlapping central region of the reaction channels 69, 73 but that in the outer regions adjoining the central regions have a structure that is shortened in a defined manner.

Figure 11:
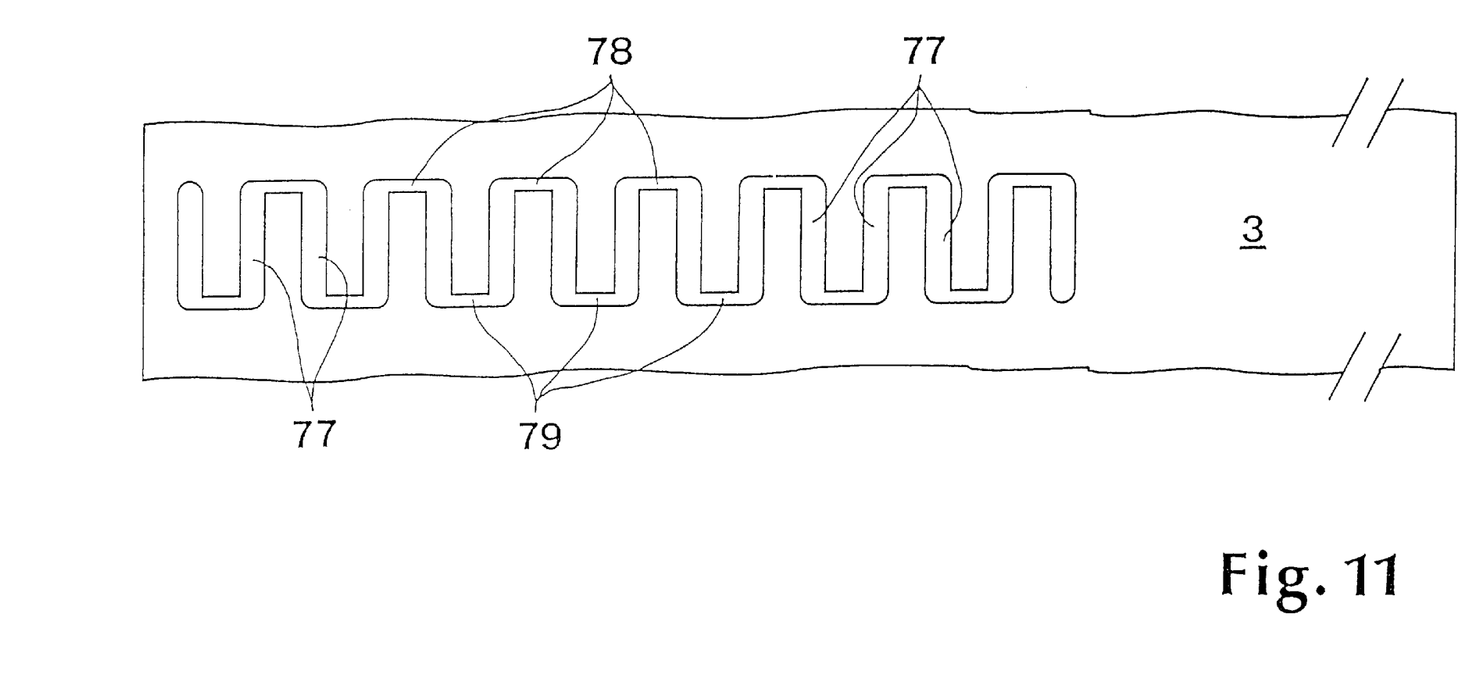
FIG. 11 is a plan view of a carrier material, in a first position before the first synthesis step, in which the zones are covered by reaction channels and intermediate channels that are arranged in one plane in the shape of a meander in accordance with the housing member shown in FIG. 3.

FIG. 11 is a plan view of the carrier film 3 which shows in outline synthesis zones 77 covered by the reaction channels 15 as well as outer reaction zones 78 covered by the first intermediate channels 16 and second outer reaction zones 79 covered by the second intermediate channels 17 as a result of mounting in a first position the first housing member 1 according to the embodiment example of a device for the synthesis of macromolecules illustrated by means of FIGS. 1 to 3.

Figure 12:
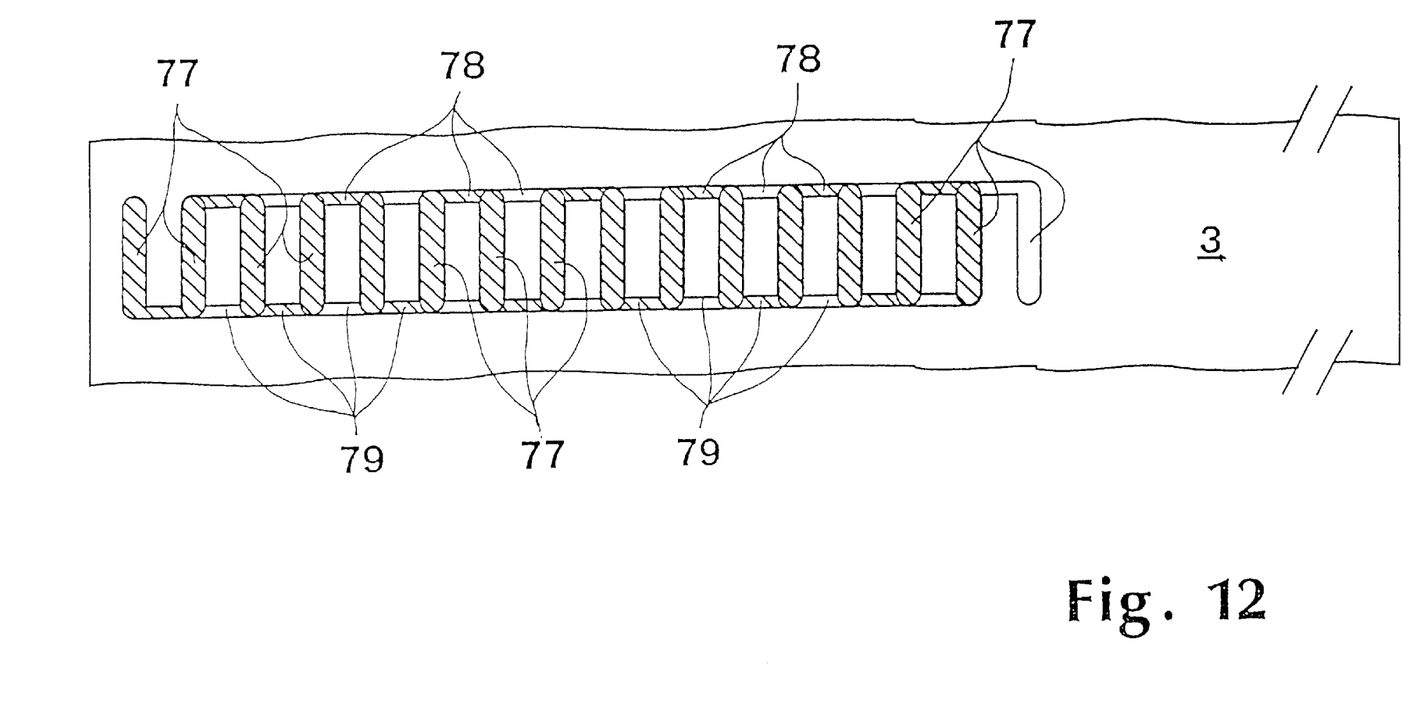
FIG. 12 shows the carrier material according to FIG. 11 in a second position before the second synthesis step.

FIG. 12 shows the arrangement according to FIG. 11 after a solvent, provided with a first reagent, has been conveyed as first reagent solution through the reaction channels 15 and the intermediate channels 16, 17 with the reaction channels 15 and the intermediate channels 16, 17, in a first position; in that arrangement the reaction channels 15 and the intermediate channels 16, 17 have been displaced with respect to the position shown in FIG. 11 by the sum of the spacing 21 between the reaction channels and the width 24 of the reaction channels. First monomers, formed on the carrier film 3 in the first synthesis step with the reaction channels 15 and intermediate channels 16, 17 in the first position are represented symbolically by diagonal hatching running from top left to bottom right. FIG. 12 also shows, in an unhatched outline, the synthesis zone 77 that is covered by a reaction channel 15 for the first time and the outer reaction zones 78, 79 that are covered for the first time, in the second position.

In that second position of the carrier film 3, for example a second reagent solution containing a different reagent is conveyed through the sequence of reaction channels 15 and intermediate channels 16, 17 following one after the other in the shape of a meander; in that second position, dimers synthesised from the first reagent and the second reagent are formed in the synthesis zones 77 that are covered for the second time, and second monomers are formed by means of the second reagent in the synthesis zone 77 that is covered by a reaction channel for the first time (shown on the right in FIG. 12), while only the first monomers formed by means of the first reagent in the first reaction step are present in the synthesis zone 77 shown on the left in FIG. 12.

Figure 13:
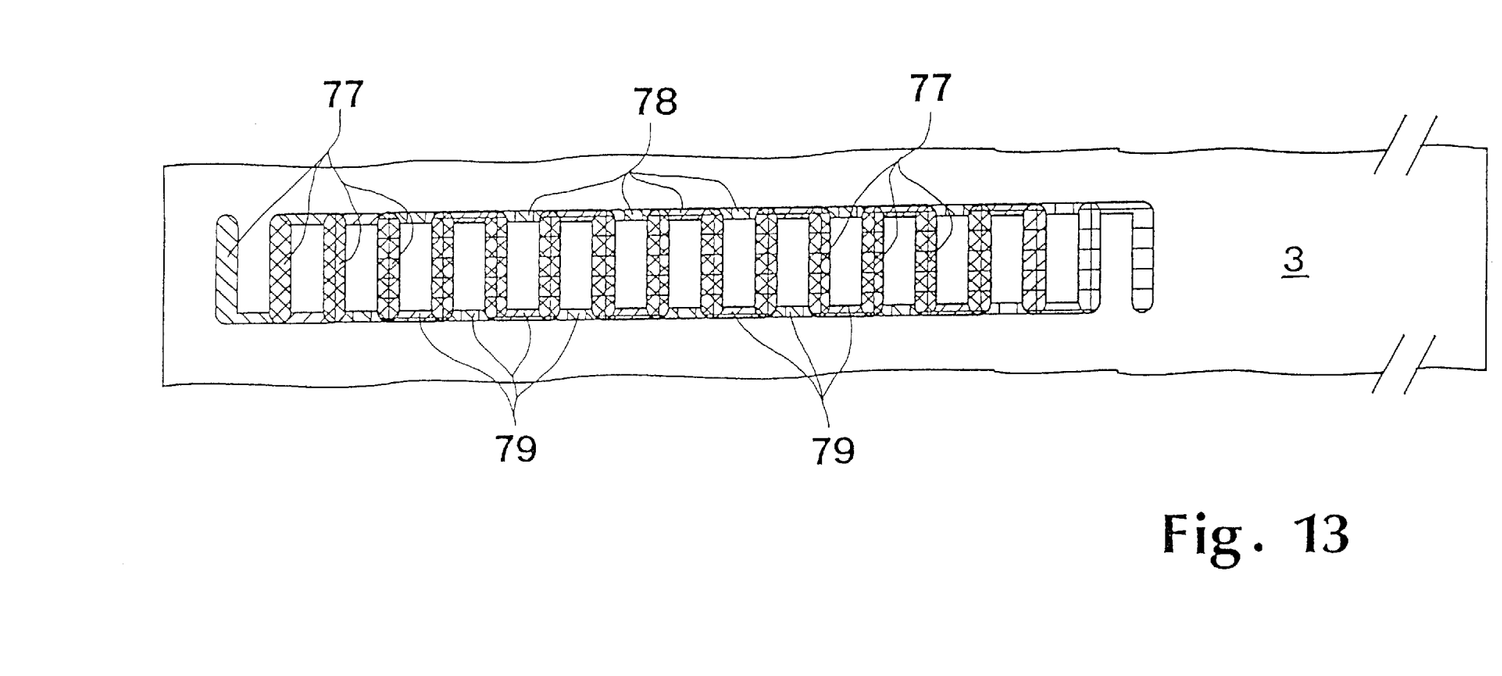
FIG. 13 shows the carrier material according to FIG. 11 and FIG. 12 in a fourth position after the fourth synthesis step has been carried out.

Corresponding to the illustrations in FIG. 11 and FIG. 12, FIG. 13 shows synthesis zones 77 and outer reaction zones 78, 79 on the carrier film 3 after four synthesis steps in which reagent solutions having four different reagents have been formed at four positions of the reaction channels 15 and the intermediate channels 16, 17, the positions being displaced with respect to one another in each case by the spacing 21 between the reaction channels and the width 24 of the reaction channels. Different kinds of hatching have been used to show different degrees of formation of the macromolecules in the synthesis zones 77 and the outer reaction zones 78, 79. In the synthesis zones 77 and outer reaction zones 78, 79 hatched only with diagonal lines running from top left to bottom right, only monomers have been formed with the first reagent conveyed through in the first synthesis step. In the outer reaction zones 78, 79 hatched only with diagonal lines running from bottom left to top right, monomers have been formed with the second reagent conveyed through in the second synthesis step. In the outer reaction zones 78, 79 hatched only with vertical lines in the illustration according to FIG. 13, third monomers have been formed in the third synthesis step by means of the third reagent conveyed through. In the synthesis zone 77 located on the right in the illustration according to FIG. 13, hatched with horizontal lines only, fourth monomers have been formed in the fourth synthesis step by means of the fourth reagent.

Differently constructed dimers, trimers and also macromolecules having four structural units are present in the remaining synthesis zones 77 and outer reaction zones 78, 79, depending on how those zones have previously been covered by reaction channels 15 and intermediate channels 16, 17, it being possible in the illustration according to FIG. 13 to identify from the superposition of the four different kinds of hatching described above the number of structural units present and which reagents have participated in their formation.

By means of further displacement of the carrier film 3 relative to the reaction channels 15 it is possible to form sequentially homologous macromolecules having an increasing number of structural units; for the formation of n oligomers having a chain length m, only m+n−1 positioning operations and synthesis steps are required. It is necessary for the number of reaction channels 15, 38, 52, 59, 69, 73 to be at least equal to the maximum chain length to be synthesised.

Figure 14:
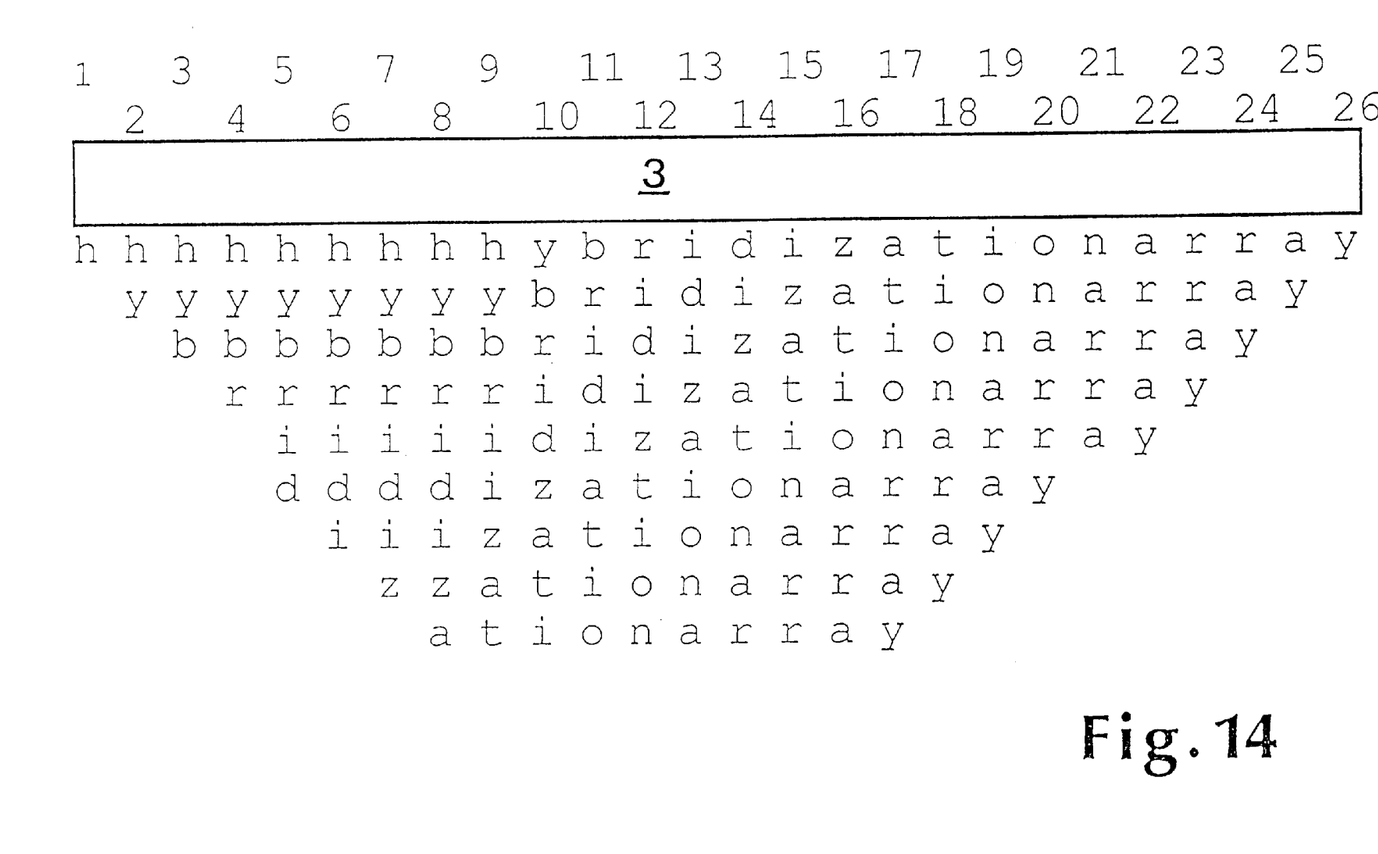
FIG. 14 is an illustrative example of the result of a synthesis of macromolecules using a housing member having nine reaction channels.

FIG. 14 shows, in a clearly symbolic illustration, a carrier film 3 on which several series of macromolecules have been synthesised which are labelled in columns by ordinal numbers 1 to 26 and comprise structural units represented by individual letters. In that synthesis a housing member having nine reaction channels was used and was displaced in eighteen synthesis steps, the reaction channels being displaced relative to the carrier film and covering the synthesis zones exactly. In the individual synthesis steps, at each position of the reaction channels reagent solutions represented by the letters a, b, d, h, i, n, o, r, t, y, z, were conveyed through one after the other in a sequence forming the word "hydridizationarray". At the positions 8 to 17 numbered in columns in the illustration according to FIG. 14, the desired ten, complete, different overlapping sequences of macromolecules constructed from nine structural units were formed. At the positions labelled by the numbers 1 to 8 and 18 to 26, analogues having fewer sequences in which the number of structural units increases by one in each of the columns 1 to 8 and decreases by one in each of the columns 18 to 26 were formed.

What is claimed is:

1. A device for the synthesis of macromolecules comprising at least one housing member comprising a plurality of reaction channels, each reaction channel having two end regions and a middle region, the plurality of reaction channels being in fluid communication with a plurality of intermediate channels which render each of the reaction channels in fluid communication with at least one other reaction channel, and further comprising at least one other housing member comprising sealing portions for covering the reaction channels, the device further comprising a carrier material disposed between the housing members thereby forming synthesis zones.

2. A device according to claim 1, wherein the distance between any two adjacent reaction channels is the same.

3. A device according to claim 2, wherein the spacing between reaction channels is greater than the width of the reaction channels.

4. A device according to claim 1 wherein the reaction channels are aligned in parallel.

5. A device according to claim 1 wherein the intermediate channels are arranged in the plane of the reaction channels and are open towards the carrier material.

6. A device according to claim 1 wherein the intermediate channels extend in the form of closed conduits outside the plane in which the reaction channels are arranged.

7. A device according to claim 1 wherein the intermediate channels open into the end regions of the reaction channels.

8. A device according to claim 1, wherein the reaction channels are the same length.

9. A device according to claim 1, wherein the reaction channels have different lengths.

10. A device according to claim 1, wherein the reaction channels are displaced with respect to one another in their longitudinal direction by a portion of their length.

11. A device according to claim 1, wherein the housing members have reaction channels arranged displaced relative to one another, there being formed between the reaction channels of one housing member sealing portions for the reaction channels of the other housing member.

12. A device according to claim 1, wherein one housing member has a guide projection that extends longitudinally and the other housing member has a guide recess that is complementary to the guide projection, for the purpose of guiding the carrier material that extends in the longitudinal direction.

13. A device according to claim 12, wherein the reaction channels extend at right angles to the guide projection.

14. A device according to claim 12, wherein the reaction channels extend at an oblique angle relative to the guide projection.

15. A device according to claim 1, wherein fixing elements are provided for pressing the housing members against one another in a releasable manner.

16. A device according to claim 1, wherein groups of the reaction channels connected to one another by intermediate channels are provided, which groups are acted upon independently of one another by a reagent solution.

17. A process for the synthesis of macromolecules which comprises employing the apparatus of claim 1, the process further comprising the steps of:

conveying reaction solutions through the plurality of reaction channels to the synthesis zones, the synthesis zones being in contact with the carrier material, the reaction channels being connected to each other by the plurality of intermediate channels and the reaction channels being in a first position relative to the carrier material;

contacting the carrier material with the reaction solutions in the synthesis zones;

displacing the reaction channels whereby the reaction channels are in a second position relative to the carrier material; and repeating the conveying, contacting, and displacing steps until a macromolecule of a desired size or structure is synthesized.

18. The process of claim 17, wherein the displacing step results in the displacement of each reaction channel to contact a synthesis zone directly adjacent to the synthesis zone previously in contact with each reaction channel.

19. The process of claim 17, wherein the displacing of the reaction channels is in a single direction.

20. The process of claim 17, wherein the repeating step is conducted at least one less time than the number of reaction channels.

* * * * *